United States Patent [19]
Gersten

[11] Patent Number: 5,384,608
[45] Date of Patent: Jan. 24, 1995

[54] METHOD FOR DISPLAYING CORNEAL TOPOGRAPHY

[75] Inventor: Martin Gersten, New York, N.Y.
[73] Assignee: Computed Anatomy Inc., New York, N.Y.
[21] Appl. No.: 44,103
[22] Filed: Apr. 8, 1993

Related U.S. Application Data

[63] Continuation of Ser. No. 778,317, Oct. 10, 1991, abandoned.
[51] Int. Cl.$^6$ .............................................. A61B 3/10
[52] U.S. Cl. .................................... 351/212; 351/247
[58] Field of Search ................. 351/212, 247; 356/376

[56] References Cited

U.S. PATENT DOCUMENTS 4,863,260 9/1989 Gersten et al. ..................... 351/212

OTHER PUBLICATIONS

Asian Pacific Journ. of Ophthal. vol. 3, No. 1, Hamano, "Fund. and Clin. Studies of Corneal Psysiology and Contact Lenses", Jan. 1991.

*Primary Examiner*—William L. Sikes
*Assistant Examiner*—Hung Xuan Dang
*Attorney, Agent, or Firm*—Howard R. Popper

[57] ABSTRACT

Color-coded corneal topographic information contained in a polar plot of plurality of different traces taken over the corneal surface, such as that disclosed in the U.S. Pat. 4,863,260, is reprocessed to present the color topographic map in a "hills and valleys", Cartesian coordinate display; polar position being presented along the x-axis and elevation being presented along the y-axis. The different circular traces are separated one from the other in a perspective dispersion to emphasize the elevation data with the more apical traces being presented at one end and the more limbal trace being presented at the other end of the perspective dispersion.

4 Claims, 3 Drawing Sheets

METHOD FOR DISPLAYING CORNEAL TOPOGRAPHY

This application is a continuation of application Ser. No. 07/778,317, filed Oct. 10, 1991 now abandoned.

FIELD OF THE INVENTION

This invention relates to the field of corneal topography and, more particularly, to the display of information about the corneal surface obtained by electronically scanning an image of the cornea.

BACKGROUND OF THE INVENTION

In recent years great strides have been made in mapping corneal contours. From the miniaturization of the Placido disc device, as taught in U.S. Pat. No. 4,772,115, to the derivation of quantitative refractive information from a two-dimensional video image of the cornea, as shown in U.S. Pat. No. 4,863,260, more accurate surgical procedures and better contact lens fitting have been made possible. In particular, the representation of corneal topography through the use of a color scale has given the ophthalmologist and the optometrist a better sense of the significance of the electronically obtained information.

In the most popular form of image acquisition apparatus, the corneal image is scanned in polar coordinates and different colors are displayed to show departures from the condition that would be exhibited by a perfectly spherical object. For example, when a perfectly spherical object is scanned, the circular disc of uniform color is displayed. When the video image of a cornea exhibiting the condition known as keratoconus is acquired by the apparatus of the aforementioned patent, the display shows a sequence of different colored and successively larger diameter regions radiating outwardly from the area of the conical apex. When a cornea exhibiting cylindrical astigmatism is scanned, two fan-shaped multi-colored areas positioned approximately 180 degrees apart but having their narrowest portions adjacent each other are displayed. Both "with the rule" and "against the rule" forms of astigmatism are readily distinguishable by the orientation of the fan-shaped colored areas.

While the color display has effectively been adopted as an industry standard and is in wide use, the color-encoded polar contour map provides only one representation of the surface contour. Because eye surgery is a particularly sensitive field requiring the exercise of considerable technical judgment and professional surgical skill that must be carried out under stressful conditions, the manner in which any information is presented to the ophthalmic surgeon must be carefully chosen. In the limited time available in the operating room the surgeon must acquire all of the data relating to the topography of the cornea, interpret that data and then exercise his professional judgment. The topographic information should be made available in a form best calculated to direct the surgeon's attention to significant surface feature. The color-coded polar may is one form of representation. Unfortunately, color coding by itself does not enable one to see the actual "hills and valleys" of the corneal surface.

In an article appearing at pp. 37–41 of the Asia-Pacific Journal of Ophthalmology of January 1991 by H. Hamano et al., a new form of displaying corneal topographic information is disclosed. In that article, the corneal topographic information contained in the polar plot, and advantageously provided by the apparatus disclosed in the aforementioned U.S. Pat. No. 4,863,260, is reprocessed to present the color topographic map in a "hills and valleys" form. This is accomplished by replotting into a Cartesian coordinate display the topographic information contained in a plurality of different circular traces taken over the corneal surface, the x-axis being used to present the polar position and the y-axis being used to plot the elevation of points. While the H. Hamano et al. article makes a useful contribution to the art of corneal information display, the direct conversion of the polar traces to Cartesian coordinates produces a welter of overlapping traces which provides no information as to which particular trace corresponds to a more apical path and which to a more limbal path.

It is an object of the present invention to provide a "hills and valleys" representation to the ophthalmic surgeon which more properly orients the traces and relates them to their radial position.

SUMMARY OF THE INVENTION

In accordance with the principles of the present invention, in one illustrative embodiment thereof, the color-coded topographic information contained in the different circular traces are separated from each other and re-presented in a perspective dispersion. In the illustrative embodiment the "first" or most apical trace is advantageously enlarged and presented at the lower end of the perspective dispersion and the more limbal traces presented successively thereafter and above. In addition, a further display is provided in which the plurality of color coded traces are presented in a modified "hills and valleys" perspective display by subtracting a constant value from the elevation coordinate information. Advantageously the constant is chosen to be the average value of the topography, e.g. the average diameter of a sphere circumscribing the patient's corneal contour.

DESCRIPTION OF THE DRAWING

The foregoing objects and features of the invention may become more apparent from the following general description when read together with the drawings, in which.

GENERAL DESCRIPTION

Figure 1:
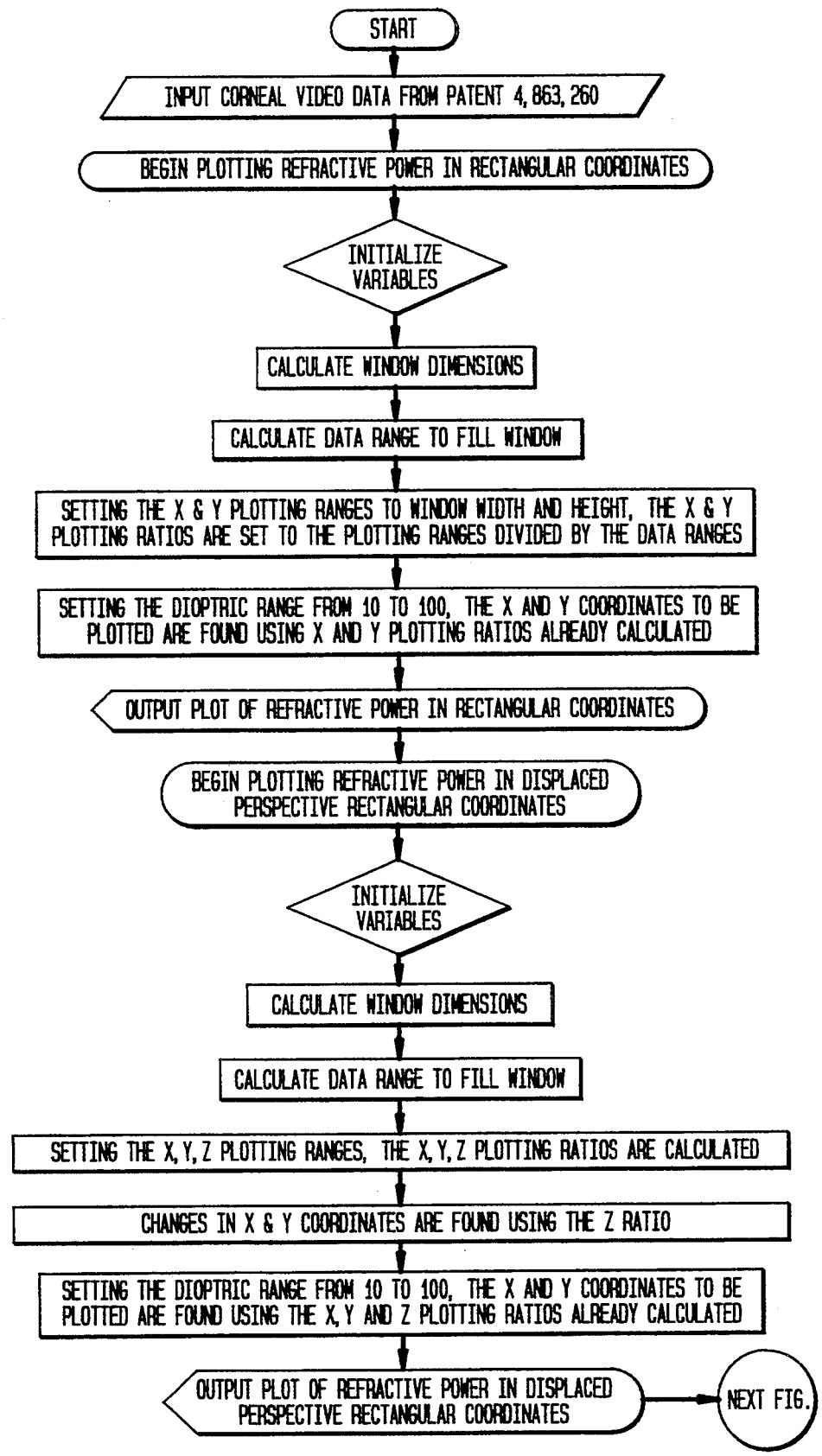
FIGS. 1 and 1A are a flow chart of the principal processing steps of my invention.
Figure 1A:
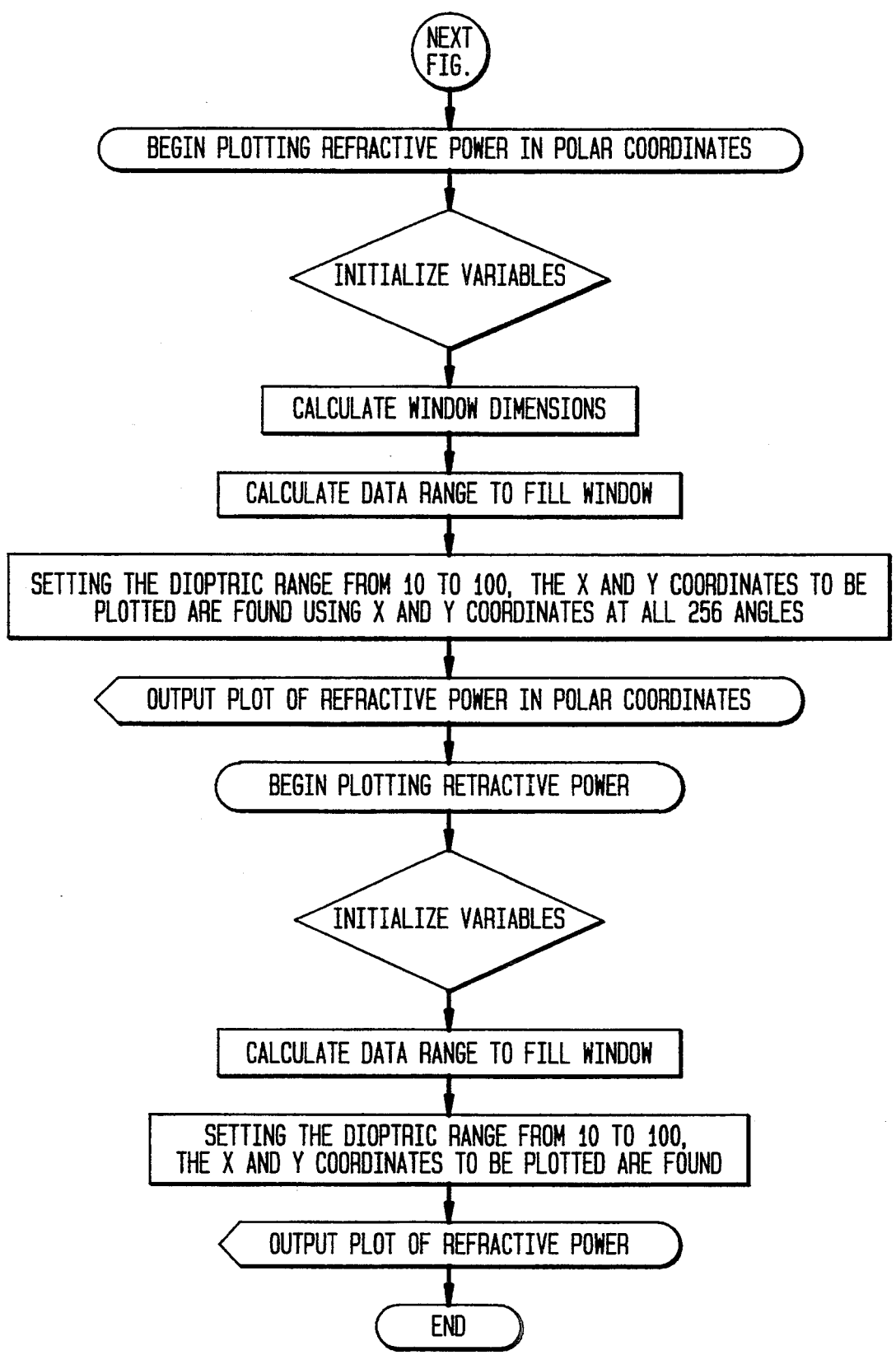

FIG. 1 is a flow chart showing the principal steps of the process of my invention. The flow chart is a guide for studying the source code for these steps which is presented in the Appendix and is written in the Pascal language.

Figure 2:
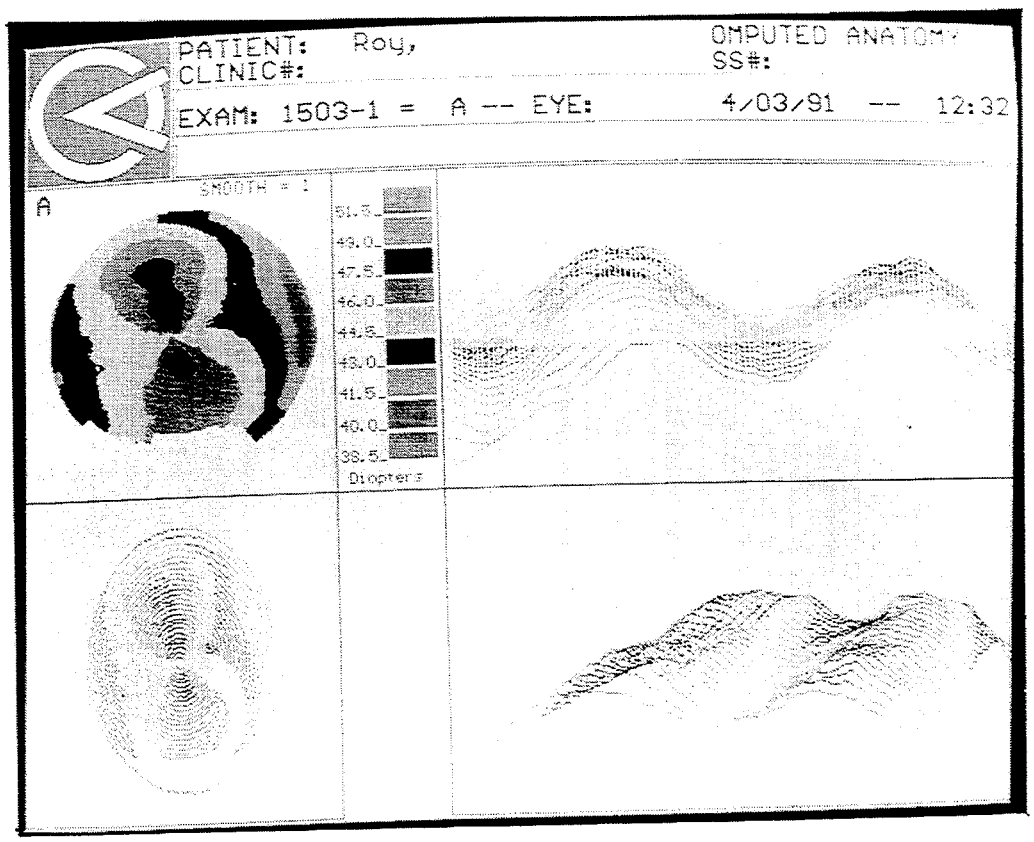
FIG. 2 is a representation of the displaced perspective topographic trace display produced by the process of my invention showing the corneal contours of a patient's cornea exhibiting a mild form of "with-the-rule" astigmatism.

FIG. 2 shows the screen display provided by my invention.

Figure 3:
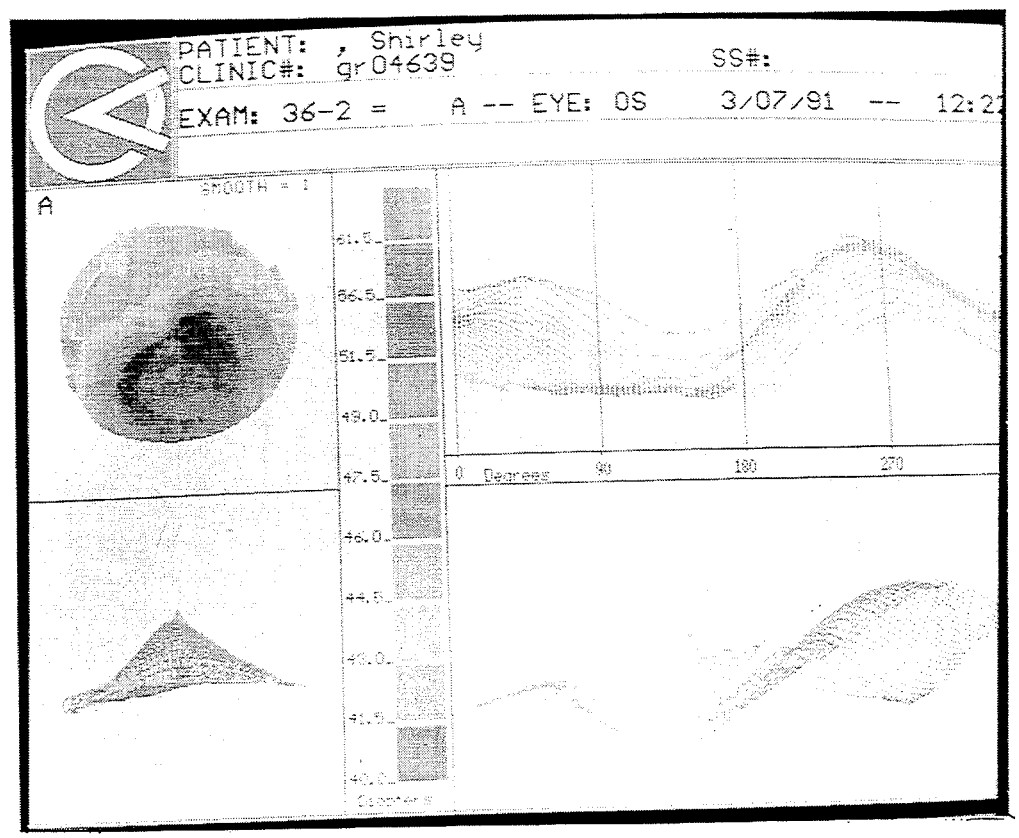
FIG. 3 is a representation of the displaced perspective topographic trace display produced by the process of my invention showing the corneal contours of a patient's cornea exhibiting keratoconus.

In the upper left-hand quadrant appears the color-coded polar topographic map disclosed in U.S. Pat. No. 4,863,260. In the upper right-hand quadrant appears the overlapping color-coded topographic trace display of the aforementioned H. Hamano et al. article. In the lower right-hand quadrant appears the perspective displaced-trace topographic display which emphasizes elevation information. Note that the lower-most trace corresponds to the most apical circular path or ring of the topographic information and that the perspective shows this path in the most magnified detail since the apical region is likely to be of great interest to the ophthalmic surgeon. In the examples of FIGS. 2 and 3, the perimeter of the first apical ring in the lower right-hand quadrant has been "stretched" so that it is approximately 140% of the path length of the corresponding trajectory depicted in the upper left-hand quadrant.

In the lower left-hand quadrant appears a modified "hills and valleys" perspective display in which the average value of a sphere circumscribing the patient's cornea has been subtracted from the elevation information to emphasize the corneal topography of greatest interest to the surgeon. The color code, red, for the contours with the highest peaks appears above the lower contours successively colored yellow through light green, darker green to blue. The lower left-hand quadrant view shows the elevation information of each separate trace set out along the y-axis, the more apical contours for the patient with keratoconus appearing above the more limbal contours.

Conclusion

Accordingly, I have described an illustrative embodiment of my invention. Numerous modifications may be employed by those skilled in the art such as substituting various degrees of perspective for the displaced traces in the lower right-hand quadrant of FIGS. 2 and 3 or even using an isometric projection in which all of the displaced traces are the same length. Further the "angle" at which the "re-assembled-displaced-trace-with-the-sphere-removed" is viewed in the lower left-hand quadrants of FIGS. 2 and 3 may be changed.

Appendix

```
PROCEDURE PLOT_REFRACTIVE_POWER_IN_RECT_COORDINATES
     (scale_type: stype; x0, y0, x1, y1: integer; min_diop,
     max_diop, mean_diop, y_range: single; iso_flag: boolean);
const
     x_data_range = 256; {theta}
     border = 8;
     first_ring = 1;
     p_inc = 0.01;
     y_plot_scale = 2.0;
     iso_y_plot_scale = y_plot_scale * 2.0;
var
     iso_delta_x, iso_delta_y, perspective: single;
     color, k, iy, iy_line, window_width, window_height, i, x,
          y, current_color, iring: integer;
     plot_x_ratio, plot_y_ratio, power, y_data_range,
          plot_z_ratio: single;
     rect_x_plot_range, rect_y_plot_range: integer;
     iso_y_plot_range, z_data_range: integer;
     iso_x_plot_range, iso_z_plot_range: single;
     iso_z_data_range, y_off: integer;
     x_lin, x_off: single;
begin
     vga_rectangle (x0, y0, x1, y1, white, 1);
     window_height := (y1 - border) - (y0 + border) + 1;
     window_width := (x1 - border) - (x0 + border) + 1;
     iso_delta_x := 0;
     iso_delta_y := 0;
     perspective := 1.0;
     y_data_range := y_range * y_plot_scale;
     case iso_flag of
     TRUE:
          begin
               z_data_range := last_ring - first_ring + 1;
               iso_x_plot_range := window_width - (cos (60 *
                    d2r) * window_height) + border;
               iso_y_plot_range := round (window_height * 0.2);
               iso_z_plot_range := window_height - 2.0 *
                    iso_y_plot_range;
```

```
                plot_y_ratio := (iso_y_plot_range /
                    y_data_range);
                plot_y_ratio := plot_y_ratio * iso_y_plot_scale;
                plot_x_ratio := iso_x_plot_range / x_data_range;
                plot_z_ratio := iso_z_plot_range / z_data_range;
                perspective := perspective + p_inc;
                y_off := round (iso_y_plot_range);
            end;
    FALSE:
        begin
            x_off := 0.0;
            y_off := window_height div 2;
            rect_x_plot_range := window_width;
            rect_y_plot_range := window_height;
            plot_y_ratio := rect_y_plot_range /
                y_data_range;
            plot_x_ratio := rect_x_plot_range /
                x_data_range;
        end;
    end; {case iso_flag}
    for iring := 1 to last_ring do
    begin
        if iso_flag then
        begin
            perspective := perspective - p_inc;
            iso_delta_y := iring * plot_z_ratio;
            iso_delta_x := iring * plot_z_ratio;
            x_off := (iso_x_plot_range - sqr(perspective) *
                iso_x_plot_range) / 2.0;
        end;
        for i := 0 to lim do
        begin
            power := powers^[iring, i];
            if (power > 10.0) and (power < 100.0) then
            begin
                x_lin := i * plot_x_ratio * perspective;
                x := x0 + border + round (x_off + x_lin +
                    iso_delta_x);
                y := y1 - y_off - (border - round
                    ((perspective * (power - mean_diop) *
                    plot_y_ratio) - iso_delta_y));
                get_color_index (scale_type, power, 0, 0,
                    current_color);
                vga_point (x, y, current_color);
            end;
        end;
    end;
end;

PROCEDURE PLOT_REFRACTIVE_POWER_IN_POLAR_COORDINATES
    (scale_type: stype; x0, y0, x1, y1: integer; min_diop,
    max_diop, mean_diop, z_range: single; iso_flag: boolean);
const
    border = 8;
    rot_x = 30 * d2r;
```

```
          rot_y = 45 * d2r;
          z_plot_scale = 2.0;
          iso_z_plot_scale = z_plot_scale * 2.0;
    var
          color, ix, iz, window_width, window_height,
          x_c, y_c, iang, x, y, current_color, iring, irad: integer;
          power, radius, t: single;
          iso_delta_x, iso_delta_y, perspective: single;
          k, iy_line: integer;
          z_data_range, plot_z_ratio: single;
          iso_z_plot_range: single;
          iso_z_data_range, z_off: integer;
       begin
          vga_rectangle (x0, y0, x1, y1, white, 1);
          window_height := (y1 - y0) + 1;
          window_width := (x1 - x0) + 1;
          x_c := x0 + (window_width div 2);
          y_c := y0 + (window_height div 2);
          radius := window_width div 2;
          net_scale := units.scale * p_scale * (radius / 190);
          for iring := 1 to last_ring do
                for iang := 0 to lim do
                  begin
                        power := powers^[iring, iang];
                        radius := ring_rad^[iring, iang];
                        if (power > 10.0) and (power < 100.0) then
                        begin
                              get_color_index (scale_type, power, 0, 0,
                                    current_color);
                              irad := round (radius * net_scale);
                              p2r (x_c, y_c, irad, iang, ix, iz);
                              vga_iso_point (x_c, y_c, ix, y_c - (power -
                                    mean_diop) * 3, iz - y_c,
                                    current_color);
                        end;
                  end;
    end;

PROCEDURE PLOT_REFRACTIVE_POWER (level: integer; scale: stype;
    last: i256; start, step: single; var blink_flag, done:
    boolean);
  var
    ix, iy, iring, iphi, current_color, previous_color, color:
    integer;
    old_radius, r0, r1, diop: single;
    key: char;
    x, y: pts4;
    laststr: words;
    on_flag: boolean;
begin
    fillchar (wt_histo, sizeof (wt_histo), 0);
    key := ' ';
    iphi := -1;
    repeat
          old_radius := 0.0;
          iphi := iphi + 1;
          if (blink_flag) then
          blink_replot_topo_message (iphi);
          initialize_segment_plot (scale, iphi, start, step,
                iring, current_color, previous_color, level, x,
                y);
```

```
            repeat
                  iring := iring + 1;
                  diop := powers^[iring][iphi];
                  get_color_index (scale, diop, start, step,
                        current_color);
                  if (previous_color <> current_color) and (iring
                        > 1) and (iring < last[iphi]) then
                  begin
                        compute_new_radius (scale, iphi, iring,
                              powers, ring_rad, start, step,
                              current_color, r0, r1);
                        load_interpolated_trapezoidal_coor (iphi,
                              r0, r1, x, y);
                        old_radius := r0;
                        color := previous_color;
                        if color > 0 then
                        begin
                              update_wt_histogram (scale, color, r0,
                                    old_radius, wt_histo);
                              vga_trapezoid (x[1], y[1], x[2], y[2],
                                    x[3], y[3], x[4], y[4], color +
                                    level, color + level);
                        end;
                        previous_color := current_color;
                        shift_trapezoidal_coordinates (x, y);
                  end;
                  if iring = last[iphi] then
                  begin
                        load_last_trapezoidal_coordinates (iphi,
                              iring, r0, x, y);
                        color := previous_color;
                        if color > 0 then
                        begin
                              update_wt_histogram (scale, color, r0,
                                    old_radius, wt_histo);
                              vga_trapezoid (x[1], y[1], x[2], y[2],
                                    x[3], y[3], x[4], y[4], color +
                                    level, color + level);
                        end;
                  end;
            until iring = last[iphi];
            if keypressed then
                  key := readkey;
      until (iphi = lim) or (key = Esc);
      if key = Esc then
            done := true;
      normal_plot_exit;
end;
```

What is claimed is:

1. A method for displaying color coded traces of corneal topography in which the topographic elevations of a plurality of points on the corneal surface are obtained by processing the data obtained from radially scanning a two-dimensional image of said surface to obtain the topographic elevations of a plurality of points along each of a plurality of substantially circular paths taken over said image, CHARACTERIZED IN THAT said data are further processed (a) to present the elevation versus polar position exhibited at points along each of said circular paths in color coded traces on a respective pair of rectangular coordinate axes, and (b) to diagonally displace the origin of each respective pair of rectangular coordinate axes from each other to portray in said color code the elevation versus polar position of said points on said surface in displacement perspective form.

2. The method of claim 1 wherein the elevations and polar positions of said points corresponding to the most apical of said circular paths is presented at one end of the diagonal of said displacement perspective and the most limbal of said paths is presented at the opposite end of the diagonal of said displacement perspective.

3. The method of claim 1 wherein the elevations and polar positions of said points corresponding to the most apical of said circular paths is presented with a greater magnification than the most limbal of said paths.

4. The method of claim 1 wherein the elevations of said points on each of said paths are represented in color coded form.

* * * * *